United States Patent [19]

Bondinell et al.

[11] Patent Number: 4,514,414
[45] Date of Patent: * Apr. 30, 1985

[54] N-SUBSTITUTED PYRROLIDINEACETIC ACIDS AND THEIR ESTERS

[75] Inventors: William E. Bondinell, Cherry Hill, N.J.; John J. Lafferty, Levittown; Charles L. Zirkle, Berwyn, both of Pa.

[73] Assignee: Smithkline Beckman Corporation, Philadelphia, Pa.

[*] Notice: The portion of the term of this patent subsequent to May 17, 2000 has been disclaimed.

[21] Appl. No.: 436,232

[22] Filed: Oct. 25, 1982

[51] Int. Cl.³ .................. A61K 31/40; C07D 207/08
[52] U.S. Cl. .................. 514/422; 548/527; 548/572; 514/428
[58] Field of Search ............... 542/400, 429; 548/572, 548/527; 424/274

[56] References Cited

U.S. PATENT DOCUMENTS

| | | | |
|---|---|---|---|
| 3,086,021 | 4/1963 | Biel | 548/527 X |
| 3,575,990 | 4/1971 | Hermans et al. | 546/216 X |
| 3,794,645 | 2/1974 | Pieper et al. | 548/527 X |
| 4,024,264 | 5/1977 | Bjork et al. | 546/222 X |
| 4,383,999 | 5/1983 | Bondinell et al. | 424/266 |

FOREIGN PATENT DOCUMENTS

| | | |
|---|---|---|
| 46-39093 | 11/1971 | Japan . |
| 46-39094 | 11/1971 | Japan . |
| 67/5136 | 1/1968 | South Africa . |
| 1313572 | 4/1973 | United Kingdom . |

OTHER PUBLICATIONS

Sam, et al., J.A.C.S., 81, (1959), pp. 710–713.
Thayer, et al., J.A.C.S., 49, (1928), pp. 2862–2869.
Lee, et al., J. Org. Chem., 39, (1974), pp. 893–902.
Rajsner, et al., C.A. 59:13936f, (1963).

*Primary Examiner*—Joseph Paul Brust
*Attorney, Agent, or Firm*—Richard D. Foggio; Joan S. Keps; Alan D. Lourie

[57] ABSTRACT

N-Substituted pyrrolidineacetic acids and their esters, useful as inhibitors of GABA uptake, are prepared by reacting an appropriate N-alkylating derivative with an esters of an N-unsubstituted pyrrolidineacetic acid followed by hydrolysis of the ester.

6 Claims, No Drawings

N-SUBSTITUTED PYRROLIDINEACETIC ACIDS AND THEIR ESTERS

This invention relates to novel N-substituted pyrrolidineacetic acids and their esters which are useful as inhibitors of neuronal and/or glial gamma-aminobutyric acid (GABA) uptake. GABA is a major inhibitory neurotransmitter of the central nervous system and is released into the synapse on nerve stimulation where it can modulate the activity of other neurons. Its actions are terminated primarily by uptake into the nerve terminal or into glial cells. Thus, inhibitors of neuronal and/or glial uptake of GABA would selectively enhance the activity of synaptically-released GABA by retarding the rate at which it is removed from the synapse. Enhancement of gabergic activity would be useful in the treatment of anxiety, epilepsy, muscular and movement disorders and mental and emotional disorders. Furthermore, these compounds may have analgesic and sedative effects as well.

The compounds of this invention are represented by the following general structural formulas:

FORMULA I

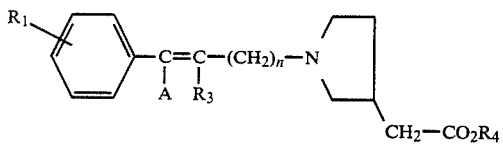

wherein:

A represents

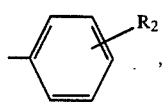

2-thienyl, 3-thienyl or cyclohexyl;

$R_1$ and $R_2$, which are the same or different, represent hydrogen, fluorine, chlorine, methyl or methoxy;

$R_3$ represents hydrogen or methyl;

n is a positive whole integer 2 or 3; and $R_4$ represents hydrogen or lower alkyl of from 1 to 3 carbon atoms;

FORMULA II

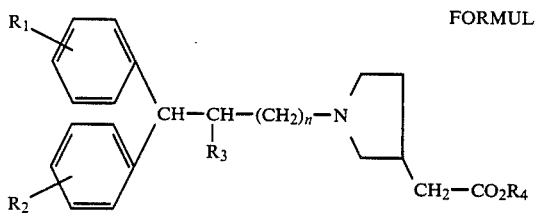

wherein:

$R_1$, $R_2$, $R_3$, $R_4$ and n are as defined above for formula I; and

FORMULA III

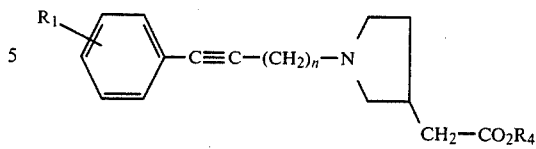

wherein:

$R_1$, $R_4$ and n are as defined above for formula I.

Particular compounds of this invention represented by formula I above are when A is

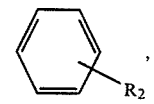

2-thienyl or cyclohexyl, $R_1$ and $R_2$ are hydrogen, fluorine, chlorine, methyl or methoxy, $R_3$ and $R_4$ are hydrogen, and n is 2; represented by formula II above are when $R_1$ and $R_2$ are hydrogen, fluorine, chlorine, methyl or methoxy, $R_3$ and $R_4$ are hydrogen and n is 2; and represented by formula III above are when $R_1$ is hydrogen, fluorine, chlorine, methyl or methoxy, $R_4$ is hydrogen and n is 2.

The pharmaceutically acceptable acid addition salts having the utility of the zwitterions of formulas I-III above, prepared by methods well known to the art, are formed with both inorganic or organic acids, for example: maleic, fumaric, benzoic, ascorbic, pamoic, succinic, bismethylenesalicylic, methanesulfonic, ethanedisulfonic, acetic, oxalic, propionic, tartaric, salicylic, citric, gluconic, lactic, malic, mandelic, cinnamic, citraconic, aspartic, stearic, palmitic, itaconic, glycolic, p-aminobenzoic, glutamic, theophylline acetic, benzenesulfonic, hydrochloric, hydrobromic, sulfuric, cyclohexylsulfamic, phosphoric and nitric acids.

Compounds of this invention may exist as geometric or optical isomers and it is intended to include herein all such isomers and mixtures thereof. The isomers may be separated by standard chromatographic or resolution techniques known to the art. Alternatively an optically active ester of an N-unsubstituted pyrrolidineacetic acid may be employed as a starting material in the reactions described hereinbelow to provide the resolved optical isomers.

The compounds of formula I are conveniently prepared by reaction of an N-alkylating derivative with an ester of an N-unsubstituted pyrrolidineacetic acid as shown in the following scheme:

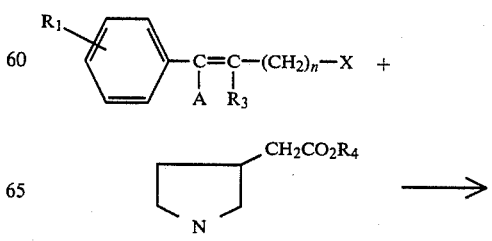

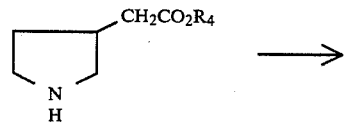

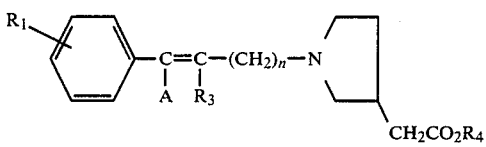

in which A, $R_1$, $R_2$, $R_3$ and n are as defined above for formula I, X is a reactive leaving group preferably halo, for example bromo, or tosyl and $R_4$ is lower alkyl of from 1 to 3 carbon atoms. Thus, a disubstituted alkenyl halide is reacted with the ester, preferably in an inert organic solvent in which the reactants are soluble such as acetone or dimethylformamide, in the presence of an alkali metal carbonate such as potassium carbonate, at reflux temperature for from 8 to 48 hours. To obtain the free acid the ester product is hydrolyzed under acidic or basic conditions, such as refluxing in concentrated hydrochloric acid for from 12 to 18 hours or refluxing in a sodium hydroxide/methanol/water solution for from ½ to 4 hours.

The disubstituted alkenyl bromide starting material is obtained from an appropriately substituted phenyl ketone by reaction with a Grignard reagent followed by treatment with hydrogen bromide in acetic acid solution.

The compounds of formula II above are similarly prepared by reaction of an ester of an N-unsubstituted pyrrolidineacetic acid with a diphenyl alkyl moiety, substituted with a halo or other leaving group or, for example by catalytic hydrogenation, such as with palladium on charcoal, of the olefinic double bond in the side chain of an appropriate compound of formula I.

The compounds of formula III above are prepared by reaction of an ester of an N-unsubstituted pyrrolidineacetic acid with a reactive ester of an appropriately substituted phenyl alkyne, substituted with a leaving group such as a tosyl group, similarly in the presence of an alkali metal carbonate such as potassium carbonate.

The free acids ef formulas II and III are similarly obtained by hydrolysis of the esters under acidic or basic conditions as described above.

The inhibition of GABA uptake produced by the compounds of this invention is measured by the ability of the active medicament to inhibit $^3$H-GABA uptake by a crude synaptosomal fraction ($P_2$) of the rat brain. In this test system, aliquots of the $P_2$ suspension are preincubated in a buffered physiological medium at 37° C. in the presence of test compound for 15 minutes. Uptake is initiated by the addition of $^3$H-GABA to a final concentration of 1 μM and terminated by filtration through a 0.45 um Millipore filter. Incubation time is 3 minutes. A compound producing a 50% or greater inhibition of GABA uptake at concentrations of 10 μM is considered to show biosignificant activity. The $IC_{50}$ value is the concentration of a compound producing a 50% inhibition of GABA accumulation. For example, a particular compound of this invention, 1-(4,4-diphenyl-3-butenyl)-3-pyrrolidineacetic acid has an $IC_{50}$ of 0.121 μM.

The compounds of this invention may be administered as pharmaceutical compositions in conventional dosage unit forms. These compositions which form a part of this invention are prepared by incorporating a compound of formulas I, II or III or a pharmaceutically acceptable acid addition salt thereof, in a nontoxic amount sufficient to produce inhibition of GABA uptake in an animal subject, with a nontoxic pharmaceutical carrier according to accepted procedures. Preferably the compositions will contain the active ingredient in an active but nontoxic amount selected from about 50 mg. to about 1000 mg. of active ingredient per dosage unit.

The pharmaceutical carrier employed may be, for example, either a solid or liquid, giving rise to a wide variety of pharmaceutical forms. If a solid pharmaceutical carrier is used, such as lactose, magnesium stearate, terra alba, sucrose, talc, stearic acid, gelatin, agar, pectin, acacia and the like, the composition can be tableted, used as a pharmaceutical powder, placed in a hard gelatin capsule or in the form of a troche or lozenge. The amount of solid carrier will vary widely but preferably will be from about 25 mg. to about 1 g. If a liquid pharmaceutical carrier is used, such as syrup, peanut oil, olive oil, sesame oil, propylene glycol, polyethylene glycol, water and the like, the composition will be in the form of a soft gelatin capsule, syrup, emulsion or a liquid suspension. Similarly the carrier or diluent may include a time delay material such as glyceryl monostearate or glyceryl distearate alone or with a wax.

The pharmaceutical preparations are made following the conventional techniques of the pharmaceutical chemist involving mixing, granulating and compressing when necessary, or variously mixing and dissolving the ingredients as appropriate to give the desired end product.

To produce inhibition of GABA uptake, a compound of formulas I, II or III, or a pharmaceutically acceptable acid addition salt thereof, usually combined with a pharmaceutical carrier, is administered internally to an animal subject in need of such inhibition in a non-toxic amount sufficient to produce said inhibition. The route of administration may be oral or parenteral. Advantageously equal doses will be administered until a desired effect is obtained, for example 2 or 3 times a day, with the daily dosage regimen being selected from about 150 mg. to about 2000 mg. of active ingredient.

The following examples illustrate the preparation of specific compounds and pharmaceutical compositions of this invention and as such are not to be construed as limitations thereof. Those skilled in the art will appreciate that other modifications of the synthetic procedures described and the use of alternative starting materials may also be employed to prepare the compounds of formulas I, II or III.

EXAMPLE 1

A solution of 147.9 g. (0.7384 mole) of 1-benzyl-3-pyrrolidineacetonitrile in 75 ml. of methanol was added dropwise to 2 l. of methanolic hydrogen chloride. The mixture was stirred for 20 hours at ambient temperature. The suspension was concentrated, chloroform added, chilled, neutralized with 10% aqueous sodium hydroxide, and extracted into chloroform. The chloroform extract was washed with water, dried over magnesium sulfate, filtered and concentrated to give methyl 1-benzyl-3-pyrrolidineacetate.

A solution of 83.9 g. (0.468 mole) of hexamic acid in 900 ml. of isopropanol was added to a solution of 109.2 g. (0.4680 mole) of the above prepared base in 100 ml. of isopropanol. The resulting solution was concentrated and ether added. The precipitated solid was filtered to give methyl 1-benzyl-3-pyrrolidineacetate hexamate, m.p. 102.5°–104° C.

The above prepared methyl 1-benzyl-3-pyrrolidineacetate hexamate was reduced in three portions, using 3.9 g. of 10% palladium on carbon in 200 ml. of absolute ethanol, for one hour at 50° C. The reaction mixture was filtered and concentrated to give methyl 3-pyrrolidineacetate hexamate, m.p. 68.5°–69.5° C.

A mixture of 44.5 g. (0.138 mole) of methyl 3-pyrrolidineacetate hexamate, 40.3 g. (0.140 mole) of 4,4-diphenyl-3-butenyl bromide and 38.2 g. (0.276 mole) of potassium carbonate in 400 ml. of acetone was refluxed for 43 hours. The mixture was chilled, filtered, concentrated and chromatographed on silica gel to give methyl 1-(4,4-diphenyl-3-butenyl)-3-pyrrolidineacetate.

A suspension of 17.9 g. (0.0512 mole) of methyl 1-(4,4-diphenyl-3-butenyl)-3-pyrrolidineacetate in 240 ml. of 5N aqueous hydrochloric acid was refluxed for 16 hours. The mixture was chilled and the aqueous phase decanted. The oily residue was taken up in 180 ml. of 1N aqueous ammonium hydroxide. The precipitate was filtered and recrystallized from water to give 1-(4,4-diphenyl-3-butenyl)-3-pyrrolidineacetic acid, m.p. 95.5°–97.5° C.

EXAMPLE 2

A solution of 0.460 g. (1.37 mmole) of 1-(4,4-diphenyl-3-butenyl)-3-pyrrolidineacetic acid in 30 ml. of absolute ethanol was reduced, using 0.15 g. of 10% palladium-on-carbon, for 1.5 hours at ambient temperature. The mixture was filtered and concentrated. A portion of the oily residue and one equivalent of maleic acid were mixed in methanol and concentrated to yield a solid which was recrystallized from isopropanol/ether to give 1-(4,4-diphenylbutyl)-3-pyrrolidineacetic acid maleate, m.p. 85°–87° C.

EXAMPLE 3

To a suspension of 4.56 g. (0.188 mole) of magnesium turnings in 20 ml. of tetrahydrofuran under argon was added dropwise 25 g. (0.208 mole) of cyclopropyl bromide in 50 ml. of dried tetrahydrofuran and the mixture refluxed for two hours. The reaction mixture was cooled and 20.3 g. (0.094 mole) of 4-chlorobenzophenone in 50 ml. of dry tetrahydrofuran was added dropwise. After refluxing for one hour the mixture was cooled in an ice bath and 130 ml. of concentrated ammonium chloride solution was added carefully. The resulting solution was poured into water, extracted with ether and the ether extract was washed with water, dried and evaporated.

The residual oil was dissolved in 200 ml. of acetic acid and treated at 20° C. with 100 ml. of acetic acid and 50 ml. of 48% hydrobromic acid. The mixture was stirred, with cooling, for 30 minutes, poured into 1 l. of water and extracted with ether. The extract was washed with water, dried, evaporated and distilled in vacuo to give (E/Z)-4-(4'-chlorophenyl)-4-phenyl-3-butenyl bromide, b.p. 203°–213° C. (0.4–0.5 mm.).

A mixture of 0.0282 mole of methyl 3-pyrrolidineacetate hexamate, 9.0 g. (0.0282 mole) of the butenyl bromide prepared above and 10 g. (0.0725 mole) of potassium carbonate in 200 ml. of acetone is refluxed for 15 hours. The reaction mixture is evaporated and chromatographed on silica to give methyl 1-[(E/Z)-4-(4'-chlorophenyl)-4-phenyl-3-butenyl]-3-pyrrolidineacetate.

The methyl ester is refluxed in 50 ml. of methanol and 20 ml. of 10% sodium hydroxide solution for one hour. The mixture is cooled, the methanol removed and the aqueous layer is acidified with 10% hydrochloric acid. The resulting solution is extracted with ethyl acetate and the dried extract is evaporated to give 1-[(E/Z)-4-(4'-chlorophenyl)-4-phenyl-3-butenyl]-3-pyrrolidineacetic acid hydrochloride.

EXAMPLE 4

To a suspension of 6.4 g. (0.266 mole) of magnesium turnings in 50 ml. of tetrahydrofuran was added dropwise 51 g. (0.268 mole) of 3-bromochlorobenzene in 100 ml. of dried tetrahydrofuran and the mixture refluxed for one hour. The cooled reaction mixture was added to 27.4 g. (0.266 mole) of benzonitrile in 100 ml. of tetrahydrofuran and refluxed for one hour. The reaction mixture was poured carefully into 100 ml. of ice/water and 10 ml. of concentrated sulfuric acid and heated on a steam bath for 30 minutes. The solution was cooled, extracted with ether, washed with water and 5% sodium bicarbonate solution, dried, evaporated and chromatographed to give 3-chlorobenzophenone (recrystallized from methanol), m.p. 83° C.

A solution of 25 g. (0.208 mole) of cyclopropyl bromide in 50 ml. of dried tetrahydrofuran was added to 4.57 g. (0.188 mole) of magnesium turnings in 20 ml. of tetrahydrofuran and the mixture refluxed for one hour. To the cooled reaction mixture was added dropwise 21 g. (0.097 mole) of 3-chlorobenzophenone and the mixture refluxed for 30 minutes. The cooled reaction mixture was treated carefully with 100 ml. of concentrated ammonium chloride solution, poured into water, extracted with ether, washed with water, dried and evaporated. The residue was dissolved in 200 ml. of acetic acid at 20° C. and a solution of 100 ml. of acetic acid and 50 ml. of 48% hydrobromic acid was added in one portion. The resulting solution was stirred for 30 minutes in an ice bath, poured into 1 l. of water, extracted with ether, washed with water, dried, evaporated and distilled in vacuo to give (E/Z)-4-(3'-chlorophenyl)-4-phenyl-3-butenyl bromide, b.p. 184°–188° C. (0.4–0.5 mm.).

A mixture of 0.0141 mole of methyl 3-pyrrolidineacetate hexamate, 3.6 g. (0.011 mole) of the butenyl bromide prepared above and 5 g. (0.0363 mole) of potassium carbonate in 100 ml. of acetone is refluxed for 15 hours. The solvent is removed from the reaction mixture and the residue suspended in water. The mixture is chromatographed on silica to give methyl 1-[(E/Z)-4-(3'-chlorophenyl)-4-phenyl-3-butenyl]-3-pyrrolidineacetate.

The methyl ester in 50 ml. of methanol and 100 ml. of 10% sodium hydroxide solution is refluxed for 30 minutes. The reaction mixture is cooled, acidified with 10% hydrochloric acid and extracted with ethyl acetate. The dried extract is evaporated to yield 1-[(E/Z)-4-(3'-chlorophenyl)-4-phenyl-3-butenyl]-3-pyrrolidineacetic acid hydrochloride.

EXAMPLE 5

To a solution of cyclopropyl magnesium bromide (prepared from 18 g., 0.15 mole, of cyclopropyl bromide and 0.15 mole of magnesium turnings in 100 ml. of dry tetrahydrofuran) at 35° C. was added 20 g. (0.1 mole) of 4-fluorobenzophenone in 50 ml. of dry tetrahydrofuran and the mixture refluxed for four hours under nitrogen. To the cooled, stirred reaction mixture was added 50 ml. of saturated ammonium chloride solution followed by 150 ml. of water and 200 ml. of ether. The organic layer was washed with water, dried and evaporated. The residue was dissolved in 300 ml. of glacial acetic acid at 10° C. and a solution of 21 g. of hydrogen bromide in 150 ml. of glacial acetic acid was added. The mixture was stirred at about 15° C. for one hour, poured into 600 ml. of ice/water and extracted with ether. The extract was washed with water and then 5% sodium bicarbonate solution. The dried solution was evaporated in vacuo and the residue distilled to give (E/Z)-4-(4'-fluorophenyl)-4-phenyl-3-butenyl bromide, b.p. 145°–150° C. (0.6–0.8 mm.).

A mixture of 15.1 g. (0.05 mole) of the butenyl bromide prepared above, 0.05 mole of methyl 3-pyrrolidineacetate hexamate, 13.8 g. (0.1 mole) of potassium carbonate and 0.2 g. of potassium iodide in 200 ml. of acetone is refluxed for 17 hours. The reaction mixture is filtered and the filtrate evaporated to give methyl 1-[(E/Z)-4-(4'-fluorophenyl)-4-phenyl-3-butenyl]- 3-pyrrolidineacetate.

The methyl ester is refluxed in 100 ml. of 5N hydrochloric acid for 17 hours. The reaction mixture is evaporated in vacuo to give 1-[(E/Z)-4-(4'-fluorophenyl)-4-phenyl-3-butenyl]-3-pyrrolidineacetic acid hydrochloride.

EXAMPLE 6

Following the procedures of Example 5, a mixture of 4,4-bis-(4'-fluorophenyl)-3-butenyl bromide, methyl 3-pyrrolidineacetate hexamate, potassium carbonate and potassium iodide in 100 ml. of acetone is refluxed for 24 hours. Similar workup of the reaction mixture gives methyl 1-[4,4-bis-(4'-fluorophenyl)-3-butenyl]-3-pyrrolidineacetate.

The methyl ester is hydrolyzed in 75 ml. of 5N hydrochloric acid to yield 1-[4,4-bis-(4'-fluorophenyl)-3-butenyl]-3-pyrrolidineacetic acid hydrochloride.

EXAMPLE 7

To a suspension of 3.9 g. (0.16 mole) of magnesium turnings in 300 ml. of dry ether was added dropwise 26.7 g. (0.16 mole) of 1-bromo-4-methoxybutane in 80 ml. of ether and the mixture refluxed for four hours. The reaction mixture was cooled and 14.6 g. (0.008 mole) of benzophenone in 100 ml. of dry ether was added dropwise. The mixture was stirred at ambient temperature for 18 hours, cautiously quenched with water and the ether layer separated. The aqueous layer was extracted with ether and the combined ether extract was dried and concentrated to give 1,1-diphenyl-5-methoxy-1-pentanol, m.p. 112°–115° C.

A mixture of the pentanol prepared as above (8.88 g., 0.0328 mole) in 132 ml. of glacial acetic acid and 66 ml. of distilled hydrobromic acid was stirred at ambient temperature for two hours and then refluxed for 90 minutes. The reaction mixture was cooled, diluted with water and extracted with ether. The ether extract was washed with 5% sodium carbonate solution, water, dried and concentrated to obtain an oil which is chromatographed on silica to yield 5,5-diphenyl-4-pentenyl bromide.

Following the procedures of Example 5, a mixture of the pentenyl bromide, methyl 3-pyrrolidineacetate hexamate and potassium carbonate in 40 ml. of acetone is refluxed for 18 hours to yield upon similar workup methyl 1-(5,5-diphenyl-4-pentenyl)-3-pyrrolidineacetate.

The methyl ester is hydrolyzed in 20 ml. of 6N hydrochloric acid to give 1-(5,5-diphenyl-4-pentenyl)-3-pyrrolidineacetic acid hydrochloride.

EXAMPLE 8

A solution of 0.0053 mole of methyl 1-(5,5-diphenyl-4-pentenyl)-3-pyrrolidineacetate in 100 ml. of ethanol and 200 mg. of 5% palladium on charcoal in 20 ml. of ethanol are hydrogenated on the Parr apparatus for about 6 hours. The reaction mixture is filtered and the filtrate concentrated to an oil, methyl 1-(5,5-diphenylpentyl)-3-pyrrolidineacetate. The ester is hydrolyzed in 100 ml. of 6N hydrochloric acid to furnish 1-(5,5-diphenylpentyl)-3-pyrrolidineacetic acid hydrochloride.

EXAMPLE 9

A solution of 4-phenyl-3-butyn-1-ol (9.33 g., 0.0638 mole) in 78 ml. of pyridine was treated with 24.8 g. (0.128 mole) of tosyl chloride at 0° C. to give the corresponding tosylate. The latter (16.0 g., 0.533 mole) is refluxed with 0.0534 mole of methyl 3-pyrrolidineacetate hexamate, 14.72 g. of potassium carbonate and 0.55 g. of potassium iodide in 267 ml. of acetone for 24 hours. Workup as described in Example 1 yields methyl 1-(4-phenyl-3-butynyl)-3-pyrrolidineacetate.

The ester (0.0126 mole) is hydrolyzed in 200 ml. of methanol and 25 ml. of 1.0 N sodium hydroxide (0.025 mole), treated with 13 ml. of 1.0 N hydrochloric acid, evaporated and the residue is recrystallized to give 1-(4-phenyl-3-butynyl)-3-pyrrolidineacetic acid.

EXAMPLE 10

Following the procedures of Example 5 the benzophenones:
- 3-methoxybenzophenone,
- 3-methylbenzophenone,
- 4-methylbenzophenone and
- 4,4'-bischlorobenzophenone are converted to the following compounds, respectively;
- 1-[(E/Z)-4-(3'-methoxyphenyl)-4-phenyl-3-butenyl]-3-pyrrolidineacetic acid hydrochloride,
- 1-[(E/Z)-4-(3'-methylphenyl)-4-phenyl-3-butenyl]-3-pyrrolidineacetic acid hydrochloride,
- 1-[(E/Z)-4-(4'-methylphenyl)-4-phenyl-3-butenyl]-3-pyrrolidineacetic acid hydrochloride, and
- 1-[4,4-bis(4'-chlorophenyl)-3-butenyl]-3-pyrrolindine-acetic acid hydrochloride.

EXAMPLE 11

To a solution of 29.6 g. (0.2 mole) of cyclopropyl magnesium bromide in 70 ml. of dry tetrahydrofuran was added over 20 minutes 18.8 g. (0.1 mole) of cyclohexyl phenyl ketone in 70 ml. of dry tetrahydrofuran under nitrogen atmosphere and at 30° C. The resulting mixture was refluxed for two hours, chilled in an ice bath and treated with 180 ml. of saturated aqueous ammonium chloride solution and 150 ml. of ether. The dried ether layer was evaporated in vacuo and the residue (18.4 g.) was dissolved in 250 ml. of glacial acetic acid. This solution was treated with 200 ml. of 20% hydrogen bromide in glacial acetic acid at 10°–15° C. and the mixture was stirred for one hour at this temperature. The reaction mixture was poured into 1 l. of water and extracted with ether. The extract was washed with sodium carbonate solution, dried and evaporated in vacuo to give (E/Z)-4-cyclohexyl-4-phenyl-3-butenyl bromide, b.p. 155°–160° C. (0.6–0.9 mm.).

A mixture (0.05 mole) of the butenyl bromide prepared above, 0.05 mole of methyl 3-pyrrolidineacetate hexamate, 0.1 mole of potassium carbonate and 0.2 g. of potassium iodide in 175 ml. of acetone is refluxed under nitrogen for 20 hours. The reaction mixture is filtered and the filtrate concentrated to give methyl 1-[(E/Z)-4-cyclohexyl-4-phenyl-3-butenyl]-3-pyrrolidineacetate.

The E/Z mixture of esters are refluxed for 17 hours in 5N hydrochloric acid. Concentration of the reaction mixture, followed by recrystallization yields 1-[(E/Z)-4-cyclohexyl-4-phenyl-3-butenyl]-3-pyrrolidineacetic acid hydrochloride.

EXAMPLE 12

Following the procedures of Example 11, 9.4 g. (0.050 mole) of phenyl 2-thienyl ketone and cyclopropyl magnesium bromide (obtained from 2.43 g. of magnesium and 3.3 g. of cyclopropyl bromide) in tetrahydrofuran were refluxed for two hours to give the corresponding cyclopropyl carbinol which is treated with 48% hydrobromic acid in glacial acetic acid to furnish (E/Z)-4-phenyl-4-(2-thienyl)-butenyl bromide, b.p. 86°-96° C. (0.015-0.025 mm.). The latter (6.52 g.) with a mixture of methyl 3-pyrrolidine-acetate hexamate (22.2 mmole), potassium carbonate and potassium iodide in 110 ml. of acetone is refluxed for 48 hours. The reaction mixture is filtered and the filtrate evaporated to leave methyl 1-[(E/Z)-4-phenyl-4-(2-thienyl)-3-butenyl]-3-pyrrolidineacetate The ester (8.42 mmole) dissolved in methanol is hydrolyzed with 8.4 ml. of 1.0N sodium hydroxide solution. The methanol is removed, 8.4 ml. of 1.0N hydrochloric acid is added and the resulting mixture evaporated to dryness. Inorganic salt is removed by filtration of an ethanolic suspension, the filtrate is evaporated and the residue is taken up in methanol. Treatment of the methanolic solution with hexamic acid gives the 1-[(E/Z)-4-phenyl-4-(2-thienyl)-3-butenyl]-3-pyrrolidineacetic acid hexamate.

EXAMPLE 13

| Ingredients | Mg. per Capsule |
|---|---|
| 1-(4,4-diphenyl-3-butenyl)-3-pyrrolidineacetic acid (as an acid addition salt) | 50 (free base) |
| Magnesium stearate | 2 |
| Lactose | 200 |

The above ingredients are mixed, passed through a #40 mesh screen, remixed and filled into #2 capsules.

EXAMPLE 14

| Ingredients | Mg. per Tablet |
|---|---|
| 1-(4,4-diphenyl-3-butenyl)-3-pyrrolidineacetic acid (as an acid addition salt) | 100 |
| Calcium sulfate, dihydrate | 75 |
| Sucrose | 25 |
| Starch | 15 |
| Talc | 5 |
| Stearic acid | 3 |

The sucrose, calcium sulfate and active ingredient are thoroughly mixed and granulated with hot 10% gelatin solution. The wetted mass is passed through a #6 mesh screen directly onto drying trays. The granules are dried at 50° C. and passed through a #20 mesh screen, mixed with the starch, talc and stearic acid, and compressed into tablets.

The capsules or tablets prepared as in Examples 13 and 14 are administered internally to an animal subject requiring inhibition of GABA uptake within the dose ranges set forth hereinabove. Similarly other compounds of formulas I, II or III can be formulated in the same manner to give pharmaceutical compositions useful in producing inhibition of GABA uptake.

We claim:

1. A compound represented by one of the formulas:

FORMULA I

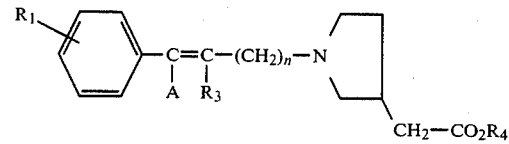

wherein:

A is

2-thienyl, 3-thienyl or cyclohexyl;

$R_1$ and $R_2$, which are the same or different, are hydrogen, fluorine, chlorine, methyl or methoxy;

$R_3$ is hydrogen or methyl;

n is a positive whole integer 2 or 3; and $R_4$ is hydrogen or lower alkyl of from 1 to 3 carbon atoms;

FORMULA II

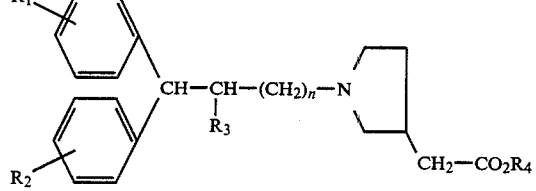

wherein:

$R_1$, $R_2$, $R_3$, $R_4$ and n are as defined above for formula I; and

FORMULA III

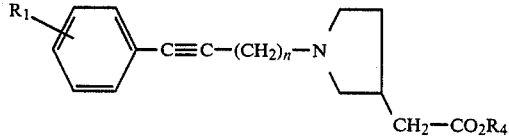

wherein:

$R_1$, $R_4$ and n are as defined above for formula I or a pharmaceutically acceptable acid addition salt thereof.

2. A compound according to claim 1 having formula I in which A is

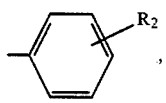

2-thienyl or cyclohexyl, $R_1$ and $R_2$ are hydrogen, fluorine, chlorine, methyl or methoxy, $R_3$ and $R_4$ are hydrogen and n is 2.

3. A compound according to claim 2 which is 1-(4,4-diphenyl-3-butenyl)-3-pyrrolidineacetic acid or a pharmaceutically acceptable acid addition salt thereof.

4. A compound according to claim 1 having formula II in which $R_1$ and $R_2$ are hydrogen, fluorine, chlorine, methyl or methoxy, $R_3$ and $R_4$ are hydrogen and n is 2.

5. A compound according to claim 1 having formula III in which $R_1$ is hydrogen, fluorine, chlorine, methyl or methoxy, $R_4$ is hydrogen and n is 2.

6. A pharmaceutical composition for inhibiting GABA uptake in dosage unit form comprising a pharmaceutical carrier and an amount sufficient to produce said inhibition of a compound of claim 1 or a pharmaceutically acceptable acid addition salt thereof.

* * * * *